(12) United States Patent
Sywe et al.

(10) Patent No.: US 10,422,750 B2
(45) Date of Patent: Sep. 24, 2019

(54) METHODS, SYSTEMS AND APPARATUSES FOR TESTING AND CALIBRATING FLUORESCENT SCANNERS

(71) Applicant: Affymetrix, Inc., Carlsbad, CA (US)

(72) Inventors: Bei-Shen Sywe, Cupertino, CA (US); Mark Borodkin, Sausalito, CA (US); Chuan Gao, Sunnyvale, CA (US); Liana Ilkova, Sunnyvale, CA (US); Devin Nguyen, San Jose, CA (US)

(73) Assignee: Affymetrix, Inc., Carlsbad, CA (US)

( * ) Notice: Subject to any disclaimer, the term of this patent is extended or adjusted under 35 U.S.C. 154(b) by 0 days.

(21) Appl. No.: 15/889,439

(22) Filed: Feb. 6, 2018

(65) Prior Publication Data

US 2018/0238802 A1     Aug. 23, 2018

Related U.S. Application Data

(62) Division of application No. 15/437,903, filed on Feb. 21, 2017, now Pat. No. 9,933,365, which is a division
(Continued)

(51) Int. Cl.
*G01N 21/64* (2006.01)
*G01N 21/27* (2006.01)

(52) U.S. Cl.
CPC ....... *G01N 21/6458* (2013.01); *G01N 21/278* (2013.01); *G01N 21/64* (2013.01); *G01N 2201/127* (2013.01)

(58) Field of Classification Search
CPC .. G01N 21/6458; G01N 21/278; G01N 21/64; G01N 2201/127
(Continued)

(56) References Cited

U.S. PATENT DOCUMENTS 2,907,882 A  10/1959 Patten
3,043,710 A   7/1962 Patten et al.
(Continued)

OTHER PUBLICATIONS

Brown, "Fluorescene microscopy-avoiding the pitfalls," Journal of Cell Science, 120: 1703-1705 (2007).
(Continued)

*Primary Examiner* — David P Porta
*Assistant Examiner* — Gisselle M Gutierrez

(57) ABSTRACT

Disclosed are calibration apparatuses for fluorescent microscopy instruments and methods of making and using them. Specifically, disclosed are calibration apparatuses with a fluorescent layer, such as photoresist, deposited on a substrate, with an optional layer of a reflective material, such as chrome. Illumination of the fluorescent and/or reflective layers, and detection and analysis of the resulting emissions allows evaluation of the instrument with respect to both reflective and fluorescent channels. Selection of appropriate fluorescent materials for the one or more fluorescent layers allows the evaluation of an instrument with respect to different fluorophores, as would be used with an instrument capable of two color detection. Inclusion of a reflective layer further allows the evaluation and calibration of all optical channels of an instrument, including the reflective channel and two or more fluorescent channels, with a single calibration apparatus for imaging criteria such as uniformity, contrast and emission signal strength.

19 Claims, 15 Drawing Sheets

Related U.S. Application Data of application No. 13/650,938, filed on Oct. 12, 2012, now Pat. No. 9,599,561.

(60) Provisional application No. 61/546,872, filed on Oct. 13, 2011.

(58) Field of Classification Search
USPC .......................................... 250/458.1, 459.1
See application file for complete search history.

(56) References Cited

U.S. PATENT DOCUMENTS

| | | | |
|---|---|---|---|
| 4,052,621 A * | 10/1977 | Haas | G01T 1/20 250/458.1 |
| 5,578,832 A | 11/1996 | Trulson et al. | |
| 5,631,734 A | 5/1997 | Stern et al. | |
| 5,834,758 A | 11/1998 | Trulson et al. | |
| 5,945,344 A | 8/1999 | Hayes et al. | |
| 5,981,956 A | 11/1999 | Stern | |
| 6,025,601 A | 2/2000 | Trulson et al. | |
| 6,140,044 A | 10/2000 | Besemer et al. | |
| 6,141,096 A | 10/2000 | Stern et al. | |
| 6,185,030 B1 | 2/2001 | Overbeck | |
| 6,201,639 B1 | 3/2001 | Overbeck | |
| 6,207,960 B1 | 3/2001 | Stern | |
| 6,252,236 B1 | 6/2001 | Trulson et al. | |
| 6,335,824 B1 | 1/2002 | Overbeck | |
| 6,399,365 B2 | 6/2002 | Besemer et al. | |
| 6,472,671 B1 * | 10/2002 | Montagu | B01L 3/0244 250/458.1 |
| 6,551,817 B2 | 4/2003 | Besemer et al. | |
| 6,597,000 B2 | 7/2003 | Stern | |
| 6,660,233 B1 | 12/2003 | Coassin et al. | |
| 6,733,977 B2 | 5/2004 | Besemer et al. | |
| 6,741,344 B1 | 5/2004 | Stern et al. | |
| 6,984,828 B2 | 1/2006 | Montagu | |
| 6,987,906 B2 | 1/2006 | Nakama et al. | |
| 7,110,629 B2 | 9/2006 | Bjorkman et al. | |
| 7,263,256 B2 | 8/2007 | Kim et al. | |
| 7,312,919 B2 | 12/2007 | Overbeck | |
| 7,406,391 B2 | 7/2008 | Miles | |
| 7,454,102 B2 | 11/2008 | Keyser et al. | |
| 7,526,170 B2 | 4/2009 | Kishima | |
| 7,574,090 B2 | 8/2009 | Shimooka | |
| 7,689,022 B2 | 3/2010 | Weiner et al. | |
| 7,871,812 B2 | 1/2011 | Weiner et al. | |
| 7,983,467 B2 | 7/2011 | Weiner et al. | |
| 8,501,122 B2 | 8/2013 | Shirazi | |
| 8,652,774 B2 | 2/2014 | Yamamoto et al. | |
| 2003/0156323 A1 | 8/2003 | Overbeck | |
| 2004/0012041 A1 | 1/2004 | West et al. | |
| 2004/0096152 A1 | 5/2004 | Nakama et al. | |
| 2004/0114853 A1 | 6/2004 | Bjorkman et al. | |
| 2005/0030601 A1 * | 2/2005 | Smith | G01N 21/278 358/504 |
| 2005/0063637 A1 | 3/2005 | Mershon et al. | |
| 2006/0105479 A1 | 5/2006 | Cave et al. | |
| 2006/0141612 A1 | 6/2006 | Yamamoto et al. | |
| 2007/0159624 A1 * | 7/2007 | Resch-Genger | G01N 21/278 356/243.1 |
| 2007/0253663 A1 | 11/2007 | Keyser et al. | |
| 2007/0262327 A1 | 11/2007 | Shimooka | |
| 2008/0085075 A1 | 4/2008 | Kishima | |
| 2009/0263923 A1 | 10/2009 | Shimooka | |
| 2011/0303027 A1 | 12/2011 | Shirazi et al. | |

OTHER PUBLICATIONS

Coling et al., "Principles and Application of Fluorescence Microscopy," Current Protocols in Molecular Biology (1998), pp. 14.10. 1-14.10.11.

Haustein et al., "Trends in fluorescence imaging and related techniques to unravel biological information," HFSP Journal, vol. 1, No. 3, Sep. 2007, pp. 169-180, http://hfspj.aip.org.

Jeff W Lichtman et al: "Fluorescence microscopy", HHS Public Access Author Manuscript, vol. 2, No. 12, Dec. 1, 2005 (Dec. 1, 2005), pp. 910-919, XP055270091, GB ISSN: 1548-7091, DOI: 10.1038/nmeth817 p. 917. line 1-line 7.

Michalet et al., "The Power and Prospects of Fluorescence Microscopies and Spectroscopies," Annual Review of Biophysics and Biomolecular Structure, 2003.32:161-182.

North, "Seeing is believing? A beginner's guide to practical pitfalls in image acquisition,"The Journal of Cell Biology, vol. 172, No. 1 (2006).

Petty, "Fluorescence Microscopy: Established and Emerging Methods, Experimental Strategies, and Applications in Immunology," Microscopy Research and Technique 70:687-709 (2007).

Waters, "Accuracy and precision in quantitative fluorescence microscopy," The Journal of Cell Biology, vol. 185 No. 7 1135-1148; www.jcb.org/cgi/doi/10.1083/jcb.100903097.

Waters et al., "Interpreting Fluorescence Microscopy Images and Measurements" Evaluating Techniques in Biomedical Research, Cell Press, pp. 37-42 (2007).

\* cited by examiner

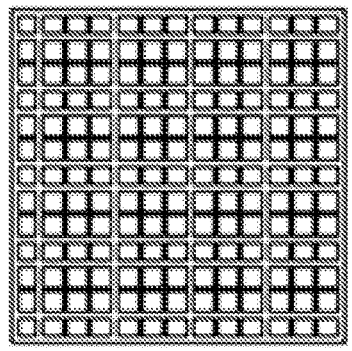
Figure 3(G)
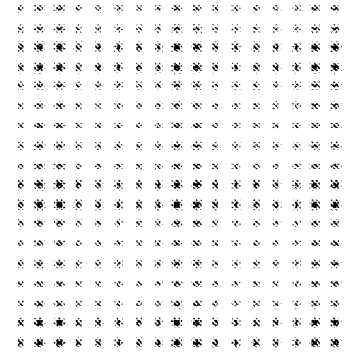
Figure 3(H)
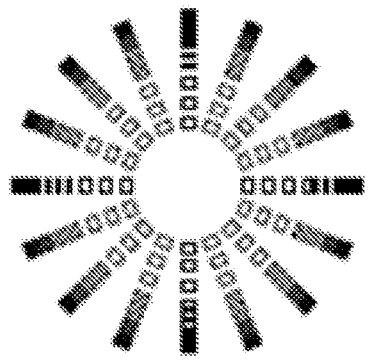
Figure 3(I)
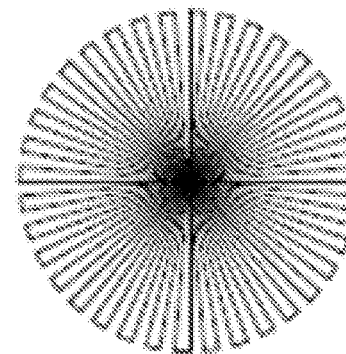
Figure 3(J)
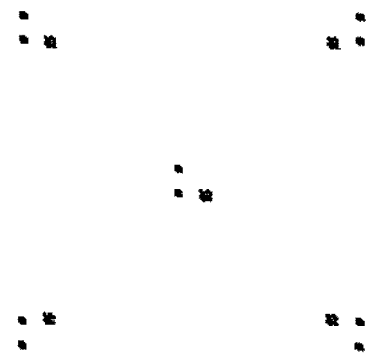
 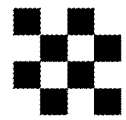
Figure 3(K)
Figure 3(L)

METHODS, SYSTEMS AND APPARATUSES FOR TESTING AND CALIBRATING FLUORESCENT SCANNERS

RELATED APPLICATIONS

The present application is a Division of U.S. application Ser. No. 15/437, 903 filed on Feb. 21, 2017 which issued as U.S. Pat. No. 9,933,365 on Apr. 3, 2018, which is a Division of U.S. application Ser. No. 13/650,938 filed on Oct. 12, 2012 which issued as U.S. Pat. No. 9,599,561 on Mar. 21, 2017, which claims priority from U.S. Provisional Patent Application No. 61/546,872, filed Oct. 13, 2011 which disclosures are herein incorporated by reference in their entirety for all purposes.

FIELD OF THE INVENTION

The presently disclosed methods, systems, and apparatuses are related to fluorescence microscopy. Provided herein are calibration apparatuses and systems and methods for using them for calibration of instruments utilized in fluorescence microscopy. The systems include a calibration apparatus, an illumination source, an optical detector, and a computer comprising a computer readable medium storing computer-executable code for controlling the system to illuminate the calibration apparatus, detect fluorescent emissions, and analyze the fluorescent emissions to identify possible calibration requirements for optimal performance.

BACKGROUND OF THE INVENTION

Fluorescent microscopy is an important aspect in many fields, especially but not limited to applications in the life sciences. Many applications involving the detection, measurement and analysis of nucleic acids, proteins, antibodies, single or multiple cells, tissue samples, and other biological materials utilize one or more fluorescent labels for detection of desired analytes. These applications include, for example, the use of nucleic acid microarrays for analysis of copy number variation, drug metabolism analysis, genome-wide or targeted genotyping, molecular cytogenetics, re sequencing, gene profiling, gene expression, gene regulation, miRNA, whole-transcript expression and profiling, and other applications. Additional applications include the analysis of proteins such as transcription factors or cytokines, nucleic acids at various levels and from various sources, including in situ with respect to single cells or tissue samples, and from cell extracts, tissue lysates, conditioned media, patient sera and plasma. Further applications involve the use of fluorescent labels as a component within various nucleic acid sequencing techniques, such as pyrosequencing, sequencing by ligation, unchained sequencing by ligation of DNA nanoballs, or sequencing by synthesis with reversible dye-terminators.

Methods, systems and apparatuses for the imaging of fluorescently labeled samples through the illumination and excitation of one or more labels and the acquisition of one or more images of the corresponding fluorescent emissions are well known in the art. For example, U.S. Pat. Nos. 5,578,832; 5,834,758; 6,025,601; and 6,252,236 to Trulson et al. disclose methods, systems and apparatuses for generating electromagnetic radiation of a particular wavelength, optics for focusing and directing the radiation, optics for collecting responsive radiation from fluorescently labeled samples, and assembling an image from the detected responsive radiation. Truism et al. additionally disclose techniques for auto-focusing to maintain the sample within the focal plane of the excitation light throughout the scanning process. U.S. Pat. Nos. 5,631.,734; 6,141,096; and 6,741,344 to Stern. et al. disclose related methods, systems and apparatuses far the detection of fluorescently labeled materials within a flow cell. Techniques utilizing galvanometer mirrors as an aspect of the radiation component are discussed within U.S. Pat. Nos. 5,981,956; 6,207,960; and 6,597,000 to Stern, Further techniques for increasing the field of view during scanning while maintaining a high scan speed and resolution are discussed within U.S. Pat. Nos. 6,185,030; 6,20,639; 6,335,824; and 7,312,919 to Overbeck.

While the quality and accuracy of the resulting images of scanned fluorescent materials is dependent upon many factors, proper adjustment of instruments for calibration and alignment is important to maintaining consistent and accurate performance. For example, U.S. Pat. Nos. 7,689,022; 7,871,812; and 7,983,467 to Weiner et al. disclose auto-focusing techniques to determine and maintain the best plane of focus for scanning Some of these techniques are based upon the use of calibration features, such as a chrome border, with the calibration and focusing being performed using, for example, detection of the reflected light from the calibration features. Additional techniques utilizing positional reference features to adjust and update a scanned image with respect to expected and actual positions within the image are disclosed in U.S. Pat. No. 7,406,391 to Miles. However, the use of metal features is generally associated with calibration of the scanning instrument with respect to alignment (e.g., exact positioning of the fluorescent target with respect to expected or optimal positions for illumination and/or detection) and with respect to related aspects such as the calibration of the relevant optical channel to be utilized for the alignment and positioning determinations.

Fluorescence microscopy has been and continues to be a field of significant research. Underlying principles of the excitation and emission of fluorophores, the operation of fluorescence microscopes, filtering options, potential light sources, and techniques to optimize fluorescence detection can be found in a variety of sources. (See, e.g., Lichtman and Conchello, "Fluorescence microscopy," Nature Methods, 2: 910-919 (2005); Haustein and Schwille, "Trends in fluorescence imaging and related techniques to unravel biological information," HFSP Journal, 1(3): 169-180 (2007); Wolf, "Fundamentals of Fluorescence and Fluorescence Microscopy, Methods in Cell Biology, 81: 63-91 (2007); Coling and Kachar, "Principles and Application of Fluorescence Microscopy," Current Protocols in Molecular Biology, 14: 14.10 (2001); Waters and Swedlow, "Interpreting Fluorescence Microscopy Images and Measurements, Evaluating Techniques in Biomedical Research, Cell Press, pages 37-42 (2007)). The associated development of new excitation sources, detectors, imaging techniques, analysis techniques and fluorescent labeling chemistries is also widely described. (See, e.g., Michalet et al., "The Power and Prospects of Fluorescence Microscopies and Spectroscopies," Annual Review of Biophysics and Biomolecular Structure, 32: 161-182 (2003); Wouters, "The physics and biology of fluorescence microscopy in the life sciences," Contemporary Physics, 47(5): 239-255 (2007)). Optimization of the overall imaging system related to fluorescence microscopy, such as utilization of light traps, improved fluorescent labels and image filtration routines, continue to be explored. (See, e.g., Petty, "Fluorescence microscopy: Established and emerging methods, experimental strategies, and applications in immunology," Microscopy Research and Technique, 70(8): 687-709 (2007); Waters, "Accuracy and precision in quantitative fluorescence microscopy, The Journal of Cell Biology, 185(7): 1135-1148 (2009)). Many aspects of fluorescence microscopy, however, remain difficult or time consuming to optimize for particular configurations of instruments, fluorophores, imaging techniques, software and the other related aspects of fluorescence microscopy. (See, e.g., Brown, "Fluorescence microscopy—avoiding the pitfalls," Journal of Cell Science, 120: 1703-1705 (2007); North, "Seeing is believing? A beginners' guide to practical pitfalls in image acquisition," The Journal of Cell Biology, 172(1): 9-18 (2006)). All of the above references are incorporated herein in their entirety for all purposes.

Many fluorescent detection instruments utilize a plurality of optical channels, with one or more channels configured for the detection of fluorescent emissions from one or more types of fluorophores. Previous approaches regarding fluorescent channel calibration include U.S. Pat. Nos. 6,472,671 and 6,984,828 to Montagu, which discuss the use of specialized calibration tools, similar dimensionally to the actual objects to be utilized with the instrument, and which possess a fluorophore layer under a non-fluorescent layer which is etched to form a desired pattern. Subsequent excitation and detection of the resultant fluorescent signal through the non-fluorescent pattern allows calibration of the one or more fluorescent channels of the relevant instrument.

Accurate and precise evaluation, calibration, and testing of fluorescent channels remain difficult in many respects. For example, creating and utilizing effective, cost-efficient fluorescent calibration targets that exhibit emissions comparable in wavelength spectra and strength to the fluorescently labeled biological materials to be subsequently analyzed continues to be a need. Additionally, the creation of fluorescent calibration targets that further possess characteristics that will be effective in optimizing performance of the instrument and overall scanning system with respect to the precise requirements which will actually be utilized remains unfulfilled. Furthermore, techniques are also needed to test and calibrate fluorescent channels while also testing and calibrating any associated reflective channels of the instrument in a compact manner. This need is further complicated by the requirement to desirably maintain effectiveness for the testing of both types of channels, and is further complicated for systems designed to evaluate and calibrate two or more different fluorescent channels, as may be present in multi-color detection instruments.

SUMMARY OF THE INVENTION

Disclosed herein are methods of evaluating fluorescence detection performance by fluorescent microscopy instruments. Suitable calibration targets to be utilized within these methods, and methods for making the calibration targets, are also disclosed. The calibration targets are useful in calibrating fluorescent microscopy instruments for one or more fluorescent channels, and in some embodiments, one or more reflective channels. Thus, preferred embodiments utilize a single calibration target with which to evaluate the performance of all optical aspects of a fluorescent microscopy instrument.

The disclosed methods for evaluation of fluorescence detection performance by a fluorescent microscopy instrument involve the illumination of an appropriate calibration target for the excitation of one or more fluorescent layers, detecting the resulting fluorescent emissions, and analyzing the fluorescent emissions to evaluate the performance of the instrument. The analysis is often performed with a computer software program with respect to pre-established criteria to guide the analysis of the emissions and to identify potential needs of the instrument for adjustment, calibration, or component replacement.

The one or more fluorescent layers comprise one or more fluorescent materials deposited on a substrate, with the materials being formed into one or more patterns in many of the disclosed embodiments. Any suitable fluorescent material may be utilized, such as fluorescent photoresist, fluorescent glass, or polymers with fluorescent properties. In many embodiments, the fluorescent materials are selected based upon their similarity in excitation and/or emission characteristics to fluorophores of interest with respect to the relevant instrument to be evaluated, such as commonly utilized fluorescent labels which are used to label biological materials that are subsequently analyzed by the instrument.

Some embodiments utilize methods and appropriate calibration targets for the evaluation of instruments with multiple fluorescent channels and which will be for use with one or more different types of fluorescent labels. To facilitate this, certain embodiments of calibration targets utilize one or more fluorescent materials which possess different emission properties with respect to different types of illumination, such as the use of different wavelength ranges for excitation. These embodiments allow the calibration of instruments with multiple fluorescent channels, such as those designed for use with a plurality of fluorescent labels with different emission wavelength spectra for a multi-color analysis and/or applications involving multiplexing.

Many embodiments additionally include a reflective layer covering at least a portion of one or more surfaces of the substrate. Materials such as chromium or chromium oxide are utilized for the reflective layer in many embodiments. The reflective layer is often patterned into one or more fiducial markers for purposes such as positional alignment of the calibration target, including translating, tilting, or rotating the calibration target and/or instrument to obtain the optimal positioning for scanning In certain embodiments, the one or more reflective layers and one or more fluorescent layers share the same pattern on the substrate, allowing the pattern to be formed within both layers simultaneously, to simplify and optimize manufacturing. Certain embodiments will further package the calibration target before actual use with the relevant instrument to be evaluated. For instance, a calibration target may be mounted upon a peg and placed on a sensor strip or plate before being utilized with an instrument.

In many embodiments, a computer software program is used to analyze the detected fluorescent emissions from the fluorescent layer and the reflection from the reflective layer of the calibration target. The analysis will often include a comparison of the detected data to one or more pre-established criteria that reflect the desired optimal results, including uniformity, contrast and emission signal strength. Based upon this analysis, software programs can identify potential aspects or components of the instrument that require further attention, such as calibration or replacement.

BRIEF DESCRIPTION OF THE DRAWINGS

The above and following features will be more clearly appreciated from the following detailed description when taken in combination with the accompany drawings. The drawings, however, are only intended to be illustrative of certain embodiments, and are not intended to be limiting.

FIG. 2(A) depicts an embodiment with both a reflective layer 120 and a fluorescent layer 130 on a substrate 110. FIG. 2(B) depicts an embodiment with only a fluorescent layer 130 on a substrate 110. FIG. 2(C) depicts an embodiment with a spacing layer 150 deposited in-between reflective layer 120 and fluorescent layer 130 on a substrate 110.

FIGS. 3(A)-3(L) depict non-limiting examples of patterns which can be created within the fluorescent layer 130, and in some embodiments, reflective layer 120, in forming calibration target 140.

DETAILED DESCRIPTION

Figure 1:
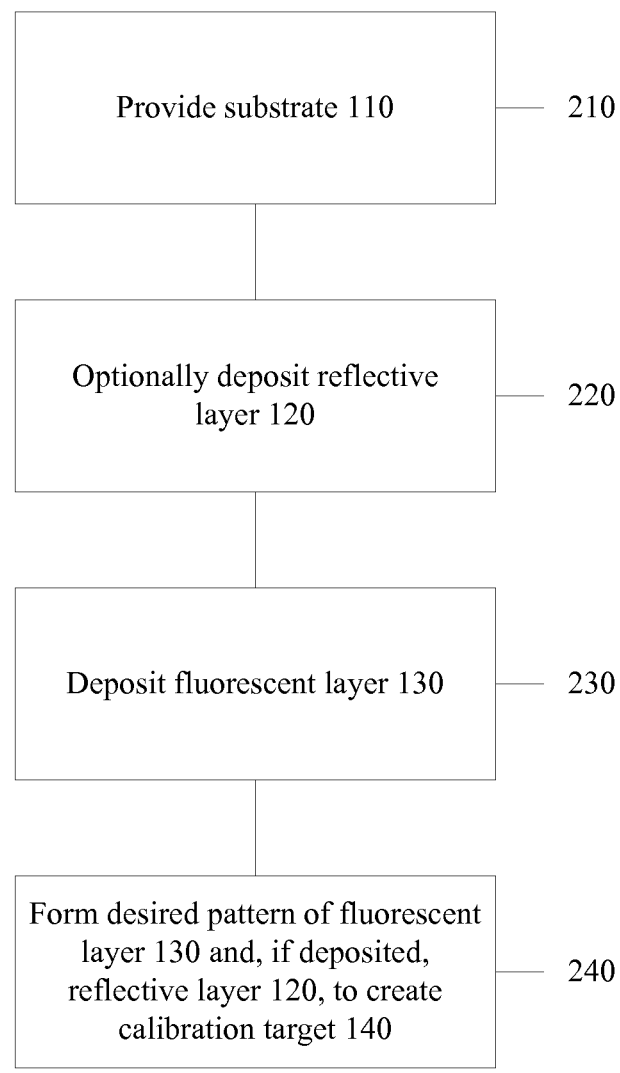
FIG. 1 depicts a flow chart illustrating the process with which certain embodiments of the calibration target 140 are manufactured through steps 210, 220, 230 and 240.

The present invention has many preferred embodiments and relies on many patents, patent applications and other references for details known to those of ordinary skill in the art to which the invention pertains. Therefore, when a reference, such as a patent, patent application, and other publication is cited or otherwise mentioned herein, it should be understood that the reference is incorporated by reference in its entirety for all purposes as well as for the proposition that is recited.

The practice of embodiments of the present invention may also employ conventional software methods and systems. Computer software products utilized with embodiments of the present invention generally include computer readable medium having computer-executable instructions for performing various steps directly or indirectly associated with aspects of the present invention. Suitable computer readable medium include floppy disk, CD-ROM/DVD/DVD-ROM, hard-disk drive (e.g., utilized locally and/or over a network), flash memory, ROM/RAM, etc. The computer executable instructions may be written in a suitable computer language or combination of several languages.

Throughout this disclosure, various aspects of the invention may be presented in a range format. It should be understood that when a description is provided in range format, this is merely for convenience and brevity, and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 2, from 1 to 2.5, from 1 to 3, from 1 to 3.5, from 1 to 4, from 1 to 4.5, from 1 to 5, from 1 to 5.5, from 2 to 4, from 2 to 6, and from 3 to 6 for example, as well as individual numbers within that range, for example, 1, 1.5, 2, 2.5, 3, 3.5, 4, 4.5, 5, 5.5, and 6. This applies regardless of the breadth of the range.

As used in this specification and the appended claims, the singular forms "a," "an" and "the" include plural referents unless the context clearly dictates otherwise. Thus, for example, reference to "a molecule" includes a plurality of such molecules, and the like.

I. Definitions

Unless defined otherwise, all technical and scientific terms used herein have the same meaning as commonly understood by one of ordinary skill in the art to which the invention pertains. The following definitions supplement those in the art, are directed to the current application, and are not to be imputed to any related or unrelated case, e.g., to any commonly owned patent or patent application. Although any compositions, systems, and methods similar or equivalent to those described herein can be used in the practice of the present invention, the preferred materials and methods are described herein. Accordingly, the terminology used herein is for the purpose of describing particular embodiments only, is not intended to be limiting, and may be further supplemented by relevant portions of this specification and by additional publications incorporated by reference.

The term "about" or "approximately" as used herein indicates the value of a given quantity varies by +/−10% of the value, or optionally +/−5% of the value, or in some embodiments, by +/−1% of the value so described.

A "calibration target" as used herein refers to an apparatus used within an instrument system for the calibration of various aspects. A calibration target may also be utilized for other purposes, such as the diagnosis of potential components of the instrument system which require calibration or replacement, quality control tests during manufacturing of the instrument, or during service repairs and maintenance for instruments already in use. A calibration target includes a substrate, upon which is deposited one or more fluorescent layers, and with certain embodiments additionally including one or more reflective layers and optionally one or more spacing layers, as each of those terms are defined herein. A calibration target may be used directly with the relevant instrument system, or combined with additional components because of factors such as size and shape compatibility with the instrument system.

A "fluorescent label" or "label" as used herein refer to a moiety that facilitates detection of a molecule through the principles of fluorescence. Non-limiting examples of fluorescent labels include organic dyes, biological fluorophores, and quantum dots. Many labels which are suitable in the context of the various embodiments disclosed herein are commercially available, such as Alexa Fluor® dyes from Life Technologies Corporation (Carlsbad, Calif.) or DyLight® dyes from Thermo Fisher Scientific, Inc. (Waltham, Mass.).

A "fluorescent layer" as used herein refers to one or more layers of one or more materials suitable for placement on a substrate and which possess fluorescent properties suitable for use with an instrument system utilized in fluorescent microscopy. The selection of materials varies from embodiment to embodiment and the desired fluorescent properties of the resulting calibration target. Preferably, the material(s) are selected so that factors such as the emission wavelength or wavelength ranges and the strength of the emissions are similar to the fluorescent material that the instrument will subsequently analyze after calibration. Thus, many embodiments possess one or more fluorescent layers which possess properties similar to biological materials which are labeled with commonly available fluorescent labels as discussed herein. The one or more fluorescent layers may be deposited upon either the substrate directly, upon a reflective layer, upon a spacing layer, or a combination of these depending on whether any reflective or spacing layers have been deposited on the entirety of one or more surfaces of the substrate, or merely on portions of one or more surfaces. Additionally, the one or more fluorescent layers may be deposited upon the entirely of one or more surfaces of the substrate or previously deposited layers on the substrate, or merely on portions. The one or more fluorescent layers may be deposited through any suitable technique for the particular embodiment and the materials utilized. Many embodiments involve the formation of one or more desired patterns within the fluorescent layer through a suitable technique. Embodiments utilizing one or more reflective layers and/or one or more spacing layers may also utilize these techniques in certain embodiments to simultaneously create all the desired patterns within the calibration target, as opposed to forming the patterns one layer at a time or only a portion of the patterns at a time. The patterns to be formed may be of any suitable size, shape, separation and variety to aid calibration of the relevant instrument.

An "instrument" or "instrument system" as used interchangeably herein refer to any suitable instrument system designed for, or suitable for use in, fluorescent microscopy. The instrument system is configured to illuminate a fluorescent molecule with light at a wavelength or range of wavelengths that is suitable to excite the particular fluorophore at issue and cause a corresponding emission of light based upon the emission characteristics of the fluorophore. Often, these systems are designed or configurable for use with particular fluorescent molecules such that the emission wavelength or range of emission wavelengths are easily distinguished from those utilized for excitation of the fluorescent molecules. The instrument system is also configured to observe and/or acquire one or more images of the fluorescent emissions. Such instrument systems are often are associated with a computer and one or more computer software programs, either directly (e.g., a built-in incorporated computer that is not designed to be separated from the instrument) or indirectly (e.g., use of a desktop computer or other remotely located computer) to operate the instrument for illumination and detection, and to optionally acquire and save images of emissions for presentation to a user.

A "reflective layer" as used herein refers to one or more layers of one or more materials suitable for placement on a substrate and which will reflect illumination for use by one or more reflective optical channels of an instrument with which the calibration target will be used. The suitability of materials or combinations of materials depends upon factors such as the type of illumination that will be utilized with respect to the reflective layer, the desired properties of the reflected light (e.g., proportion of illumination that is reflected, wavelengths of reflected light), the wavelength(s) which the instrument will utilize from the reflective light (e.g., if the instrument utilizes a filter), and other factors. The formation of the desired patterns with the reflective layer(s) may be done via any suitable technique. A reflective layer is not utilized within all embodiments of the calibration targets disclosed herein.

A "spacing layer" as used herein refers to a material or group of materials within a calibration target that is optionally deposited on the substrate or between layers that are deposited on the substrate (e.g., between a reflective layer and a fluorescent layer, between two different reflective layers, between two different fluorescent layers).

A "substrate" as used herein refers to a material or group of materials having a rigid or semi-rigid surface or surfaces.

A "target" or "target material" or "analyte" or "sample" as used interchangeably herein refers to a molecule or group of molecules to be detected by an instrument or instrument system, often through detection of a fluorescent label directly or indirectly associated with the molecule or group of molecules. In many aspects the target is a biological material such as nucleic acids, polypeptides or antibodies.

II. Specific Embodiments

Various embodiments are contemplated herein relating to methods, systems and apparatuses for the testing, evaluating and calibrating of fluorescent channels of scanners, microscopes and other instruments that utilize one or more fluorescent channels for the detection, measurement, and/or observation of fluorescent materials. Many embodiments are suitable for use with fluorescent scanners and microscopes utilized in the life sciences for the detection and measurement of fluorescently labeled biological materials. Additionally, many embodiments are combined with, or are suitable for combination with the testing, evaluating, aligning and calibrating of one or more reflective channels of scanners, microscopes and other instruments for purposes such as positional alignment and calibration of the scanner or microscope with respect to a fluorescently labeled target. It is to be understood that the following description, including any examples provided herein, is intended to be illustrative and not restricted to the following embodiments. The examples and embodiments herein are for illustrative purposes and serve as non-limiting examples, as many variations of the invention will be apparent to those of skill in the art upon reviewing the entire specification, including the appended claims, and the full scope of equivalents to which the claims are entitled.

Creation of calibration target 140 for subsequent use in the calibration of at least one fluorescent channel of a suitable instrument may follow, for example, the flowchart depicted in FIG. 1. Suitable instruments include microscopes and scanning devices designed to illuminate a fluorophore with one or more wavelengths of light to cause the emission of fluorescence, with subsequent observation and/or capture of the fluorescent emissions through an objective lens and/or camera. Such instruments are widely available commercially from, for example, Nikon Corporation (Tokyo, Japan) or Olympus Corporation (Tokyo, Japan). Some embodiments are compatible for use with instruments configured for the detection of fluorescent labels utilized in conjunction with instruments and systems for analysis of biological materials (e.g., nucleic acids, proteins), such as the GeneAtlas® Personal Microarray System, GeneTitan® Instrument or GeneTitan® Multi-Channel Instrument (Affymetrix, Inc., Santa Clara, Calif.), the MS 200 Microarray Scanner (Roche NimbleGen, Inc., Madison, Wis.), the SureScan Microarray Scanner (Agilent Technologies, Inc., Santa Clara, Calif.), or the HiScan™ System, iScan System, BeadXpress™ Reader, HiSeg™ Sequencing System, MiSeg™ System or Genome Analyer$_{IIx}$ System (Illumina, Inc., San Diego, Calif.).

In step 210, a substrate 110 is provided. Substrate 110 comprises one or more suitable materials or groups of materials having a rigid or semi-rigid surface or surfaces. In many embodiments, at least one surface of the substrate will be substantially flat (e.g., glass slides, silicon wafers), although in some embodiments the substrate may have various features, associated directly or indirectly, such as pegs, wells, pins, etched trenches, channels, flow cells, flow cell channels, raised regions or other features which may be structurally designed or inherent to the relevant material or materials. Non-limiting examples of potential substrate materials include glass, Si, Ge, GeAs, GaP, $SiO_2$, $SiN_4$, other silicon based materials, fused silica, fused quartz, polyvinylidene fluoride, polycarbonate, other polymers, and combinations of these and other suitable materials known in the art. Suitable substrates may also be manufactured from two or more different components, with each component made out of one or more suitable materials. Each component may or may not have different structural features and design aspects. A non-limiting example of a multi-component substrate is a glass slide component within a silicon based frame.

Step 220 involves an optional step, where a reflective layer 120 may be deposited upon substrate 110. Reflective layer 120 may also comprise one or more layers of any suitable material or combination of materials which will reflect illumination for subsequent use by one or more reflective optical channels of an instrument with which the calibration target will be used for purposes such as positional alignment and calibration based upon, for example, reflectance from fiducial alignment markers comprising reflective layer 120. The optimal material or materials may vary depending upon the embodiment, and the desired strength and wavelengths of the reflection signal based upon the type of illumination used by the instrument. For example, instruments may employ light sources such as light emitting diodes, lamps (e.g., xenon arc lamps, mercury-vapor lamps), or lasers (e.g., krypton, argon, copper vapor, Nd:YAG, helium neon). The power output of the illumination will vary greatly depending upon the particular system, and may be, for example, from 1-25 milliwatts, such as 1, 2, 3, 4, 5, 7.5, 10, 15, 20, or 25 milliwatts. These non-limiting examples should not be construed as to be limiting, as various embodiments of calibration targets disclosed herein may be modified and adjusted for use with various instrument systems, including those with illumination power ranges within the above range (e.g., 12.5, 22.5 mW) or outside of the range (e.g., 0.75, 30, 50, 100). Furthermore, the illumination may comprise light at various wavelengths or ranges of wavelengths, as may be optimal for a particular instrument or instrument system. Many embodiments of reflective layers are utilized with illumination wavelength(s) within the visible light range of electromagnetic radiation (e.g., from about 380 nanometers to about 740 nanometers). Depending on the type of light source and the optional use within the system of additional optical components (e.g., filters, filter wheels, beam splitters), the illumination may comprise a single wavelength (e.g., 420, 490, 520, 550, 650), a range of wavelengths (e.g., 470-490, 525-550, 570-610), or combinations of these. The selection of the material for reflective layer 120 will depend in large part upon the desired wavelength or wavelength range at which the reflectance will be used for subsequent calibration of the optical channel(s), auto-focusing, etc. For example, if the particular optics of the relevant instrument favor utilizing fiducials with high reflectance with respect to light of 590 nanometers, then the material(s) with which those fiducials are made should possess a high reflectance with respect to such light, including other relevant factors such as the properties of the particular type of instrument, the properties of fluorescent layer 130 (if fluorescent layer 130 will be deposited on top of relevant portions of reflective layer 120 that will be utilized by the instrument), and the properties of any spacing layers 150 which are utilized within calibration target 140. Non-limiting examples of materials suitable in certain embodiments include metals such as chromium, chromium oxide, silver, gold, nickel, aluminum, a material with a chrome plating layer, or mixtures or combinations of these (e.g., a bottom layer of chromium with a top layer of chromium oxide). In some embodiments, step 220 comprises depositing reflective layer 120 onto substrate 110 using physical vapor deposition techniques. In a preferred embodiment, sputter deposition is utilized, but other embodiments may employ alternative sputtering techniques, other physical vapor deposition techniques, or other suitable methods employing, for example, chemical vapor deposition, vacuum deposition, or, depending upon the material, other techniques such as spin coating or dip coating. Reflective layer 120 may alternatively comprise a single layer of a material or group of materials, or more than two layers of materials or groups of materials. For example, reflective layer 120 may be formed by using sputter deposition to deposit a layer of chromium before a second layer of chromium oxide is deposited. Reflective layer 120 may be deposited on an entire surface, on multiple surfaces, or selected portions of one or more surfaces of substrate 110. The thickness of reflective layer 120 will vary depending upon the embodiment and factors such as the material composition of substrate 110, the material composition of reflective layer 120, the material composition of fluorescent layer 130, the desired optical density of reflective layer 120, the properties of the one or more optical channels of the instrument for which reflective layer 120 will be utilized, the thickness of fluorescent layer 130 in relation to the thickness of reflective layer 120, and other factors. Suitable thicknesses for reflective layer 120 in some embodiments range from 0.025 μm to 5.0 μm, such as 0.025 μm, 0.05 μm, 0.1 μm, 0.2 μm, 0.3 μm, 0.4 μm, 0.5 μm, 0.75 μm, 1.0 μm, 1.5 μm, 2.5 μm, and 5.0 μm. Certain embodiments will utilize other thicknesses within this range, such as 0.6 μm or 3.0 μm, or a thickness outside of this range, such as 0.01 μm or 6.0 μm, if required for the embodiment based upon, for example, the factors affecting thickness recited above. In a preferred embodiment, reflective layer 120 comprises a chromium layer topped with a thin layer of chromium oxide to produce a reflective layer 120 that is 0.1 μm thick with an optical density of 3.0. In some embodiments, decreasing the thickness of the material(s) utilized for reflective layer 120 improves the resulting reflectance as the corresponding optical density decreases toward 1.

It should be noted that reflective layer 120 is an optional component, and not all embodiments will include a reflective layer 120. Alternative embodiments of calibration target 140 may not utilize reflective aspects for calibration of reflective oriented channels of the instrument, with the need and benefits of such calibration, auto-focusing and resulting positional adjustments being performed by, for example, other calibration devices or by reflective aspects which are utilized when the fluorescently labeled target material of interest is actually analyzed (e.g., a reflective layer or fiducial markers on a substrate with which the labeled target is associated). Still other embodiments may utilize alternate approaches such as built-in reflective layers or fiducial markers within substrate 110, or adding fiducial markers to calibration target 140 at some later point (e.g., after fluorescent layer 130 has been deposited, or after step 240 has been performed to form the desired pattern of fluorescent layer 130). Non-limiting examples of possible fiducial markers which can be added to calibration target 140 include those illustrated in FIGS. 5(A) through 5(D). Still other embodiments utilize one or more layers of a single material deposited on substrate 110, the patterns of which are used for calibration of both reflective and fluorescent channels. Such materials must possess sufficient reflectivity for use with the reflective channel(s) while additionally being able to absorb and then fluoresce light at sufficient signal levels for use with the relevant instrument, and selection of such materials will weigh heavily upon the characteristics of the instrument, such as its sensitivity and contrast abilities.

Step 230 involves depositing fluorescent layer 130. Fluorescent layer 130 may comprise any suitable material or combination of materials, where at least one material possesses fluorescent properties suitable for use in conjunction with the one or more optical channels of the relevant instrument which are utilized to detect fluorescent emissions of the desired target material. The optimal material or materials will vary depending on the embodiment and various factors. For example, the number and characteristics of fluorescent emission wavelengths or wavelength ranges to be measured from the target after appropriate excitation by the instrument system will guide the selection of appropriate material(s). Other factors, such as the properties of the instrument system (e.g., possible illumination wavelengths, detection filters to be utilized), and the number and types of different instruments with which a particular calibration target 140 will be utilized, will also guide the selection of appropriate material(s). For example, if the target possesses a fluorescent label of Cy3, fluorescent layer 130 would desirably possess fluorescent emission properties in the 550-600 nm range to provide a calibration target 140 with fluorescent properties similar to that of the target. Furthermore, if the relevant instrument is utilized with a plurality of dyes, such as utilizing fluorescein isothiocyanate in addition to Cy3, then fluorescent layer 130 would desirably also possess fluorescent emission properties in the 500-550 nm range as well to simulate the emission spectrum of fluorescein isothiocyanate. Additionally, the one or more fluorescent layers 130 of a calibration target 140 enable, in some embodiments, the use of a single calibration target 140 for a multi-fluorescent channel instrument. Other embodiments employ one or more fluorescent layers 130 which are suitable, either separately or in combination, with multiple excitation source and/or wavelength systems, and/or systems with multiple excitation and/or emission filters.

Moreover, the resulting fluorescent emissions from fluorescent layer 130 are desirably of strength comparable to the expected emissions from the labeled target interest to further aid in a relevant calibration of the one or more fluorescent channels. In some embodiments, a plurality of fluorescent layers 130 may be utilized, with at least some of the layers possessing different fluorescent properties from the other layers. Certain embodiments employ from 2-5 distinct fluorescent layers. This range should not be construed to be limiting, as many embodiments utilize only one fluorescent layer, and other embodiments may optionally employ more than 5 layers. Alternatively, a first type of a fluorescent layer 130 may be deposited for eventual use within select portions of the calibration target 140 while a second type of fluorescent layer 130 with different properties is deposited for use within other portions of calibration target 140. Non-limiting examples of suitable materials for fluorescent layer 130, depending on the embodiment and the relevant instrument, include photoresist materials possessing fluorescent properties such as SU-8, fluorescent glass, various polymers with fluorescent properties such as poly(2-vinylnaphthalene), poly(2-naphthyl methacrylate), poly[N-(1-naphthyl)-N-phenylacrylamide], other polymers with fluorescent properties, and combinations of these. Photoresist material with fluorescent properties suitable for use within various embodiments is available commercially from, for example, AZ Electronic Materials (Stockley Park, Middlesex, United Kingdom). Fluorescent polymers suitable for use within certain embodiments are also available commercially from, for instance, Sigma-Aldrich Corporation (St. Louis, Mo.).

An advantage to utilizing photoresist materials with the desired fluorescent characteristics is that the photoresist may often be subsequently patterned using standard lithography techniques. As with reflective layer 120, fluorescent layer 130 may be deposited by any method which is suitable for the particular material(s) used within the embodiment at issue, including, for example, spin coating, dip coating, chemical vapor deposition, physical vapor deposition, or vacuum deposition. In preferred embodiments the photoresist material comprising fluorescent layer 130 is deposited by spin coating.

Figure 2A:
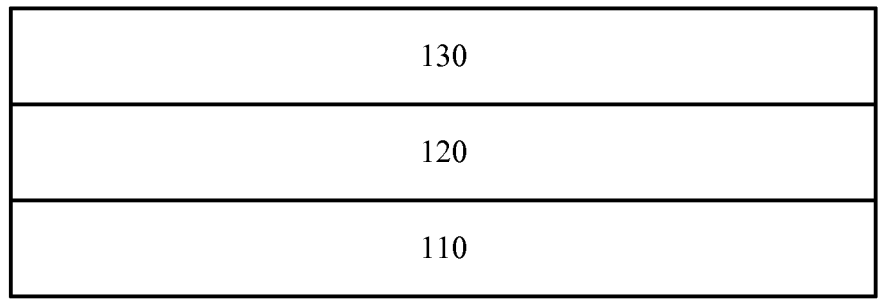
FIGS. 2(A)-2(C) illustrate three exemplary non-limiting embodiments of calibration targets from a vertical cross-sectional view.
Figure 2B:
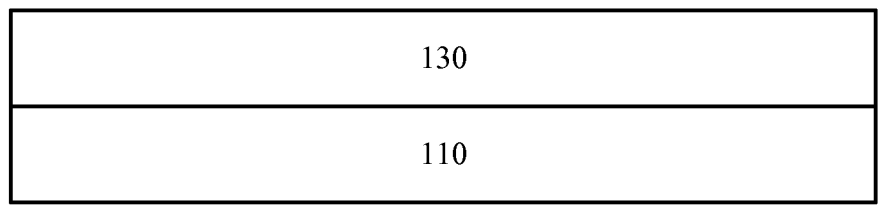

If reflective layer 120 was deposited onto substrate 110 on one or more surfaces, then fluorescent layer 130 may, in some embodiments, be at least partially deposited on top of reflective layer 120 while leaving other areas of reflective layer 120 exposed. Other embodiments may deposit fluorescent layer 130 entirely on top of reflective layer 120, which is illustrated in FIG. 2(A). If, however, a reflective layer 120 was not deposited onto substrate 110, then fluorescent layer 130 may be deposited directly onto substrate 110.

Figure 2C:
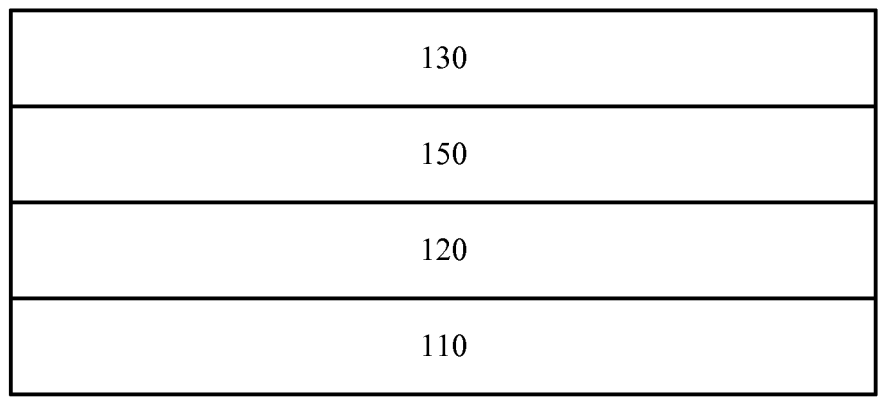
Figure 3A:
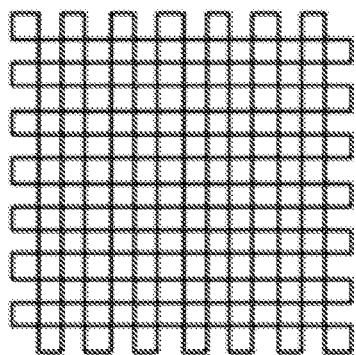
Figure 3B:
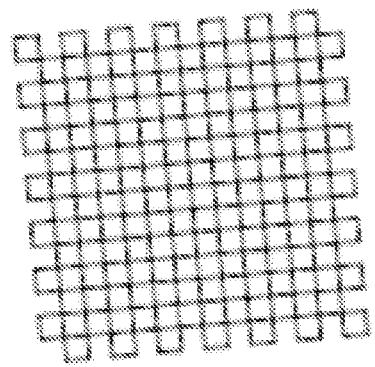
Figure 3C:
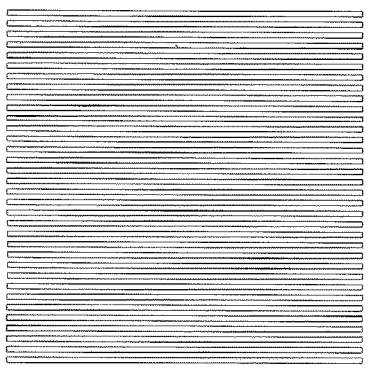
Figure 3D:
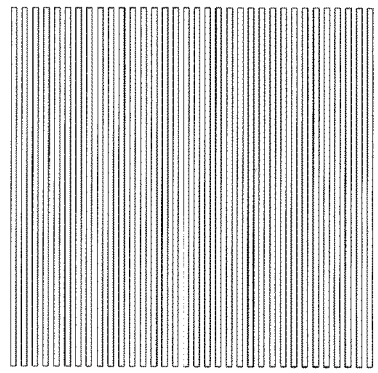
Figure 3E:
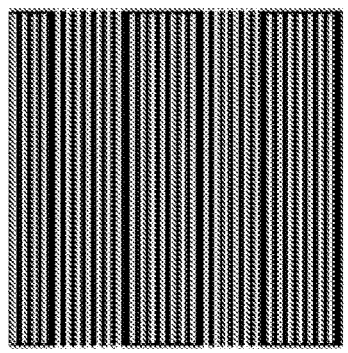
Figure 3F:
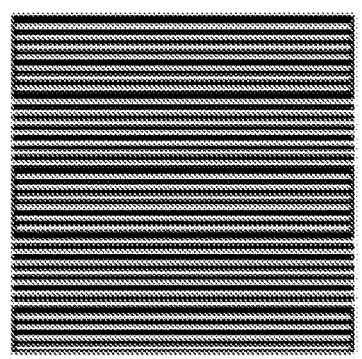

Furthermore, certain embodiments may optionally utilize one or more spacing layers 150 between substrate 110 and reflective layer 120, reflective layer 120 and fluorescent layer 130, or substrate 110 and fluorescent layer 130 (when a reflective layer 120 is not deposited). Thus, embodiments of calibration target 140 may utilize 0, 1, 2 or more spacing layers 150, with each layer comprising one or more layers of one or more materials. Suitable thicknesses for spacing layer 150 in some embodiments range from 0.025 µm to 5.0 µm, such as 0.025 µm, 0.05 µm, 0.1 µm, 0.2 µm, 0.3 µm, 0.4 µm, 0.5 µm, 0.75 µm, 1.0 µm, 1.5 µm, 2.5 µm, and 5.0 µm. Certain embodiments will utilize other thicknesses within this range, such as 0.6 µm or 3.0 µm, or a thickness outside of this range, such as 0.01 µm or 6.0 µm. The one or more spacing layers 150 may serve purposes such as aiding the manufacturing process (e.g., facilitating the formation of the desired pattern of fluorescent layer 130 within step 240), increasing efficiency of the resulting calibration target 140 based on factors such as the optical characteristics of the materials used within calibration target 140 or the optical detection properties of the relevant instrument, or in promoting adhesion of the different layers (e.g., if the material(s) used within reflective layer 120 do not naturally adhere to the material(s) used within fluorescent layer 130). Some embodiments utilizing photoresist for fluorescent layer 130 may utilize a spacing layer 150 of polyimide to aid in the adhesion of the polyimide to the reflective layer 120. The purpose of spacing layer 150 in a particular embodiment will guide the selection of an appropriate material. For instance, if a spacing layer 150 is utilized between reflective layer 120 and fluorescent layer 130, a material for spacing layer 150 may be selected which is substantially optically transparent in order to avoid a substantial reduction in the reflectance of reflective layer 120 with respect to the one or more reflective channels of the instrument. Such an embodiment with spacing layer 150 is illustrated in FIG. 2(C).

Step 240 involves the formation of a desired pattern of fluorescent layer 130. Embodiments utilizing a reflective layer 120 may also have a pattern formed within reflective layer 120 during step 240 as well, or alternatively utilize two or more steps to create the patterns within fluorescent layer 130 and reflective layer 120. The formation of the desired pattern may be achieved through any suitable technique, such as photolithography, electron beam lithography, optical maskless lithography such as direct laser writing or interference lithography, ion beam lithography, destructive scanning probe lithography, plasma etching, wet etching, or other techniques known in the art. Certain embodiments utilizing a fluorescent layer 130 comprising photoresist and a reflective layer 120 comprising chromium may preferably utilize contact lithography.

Figure 4A:
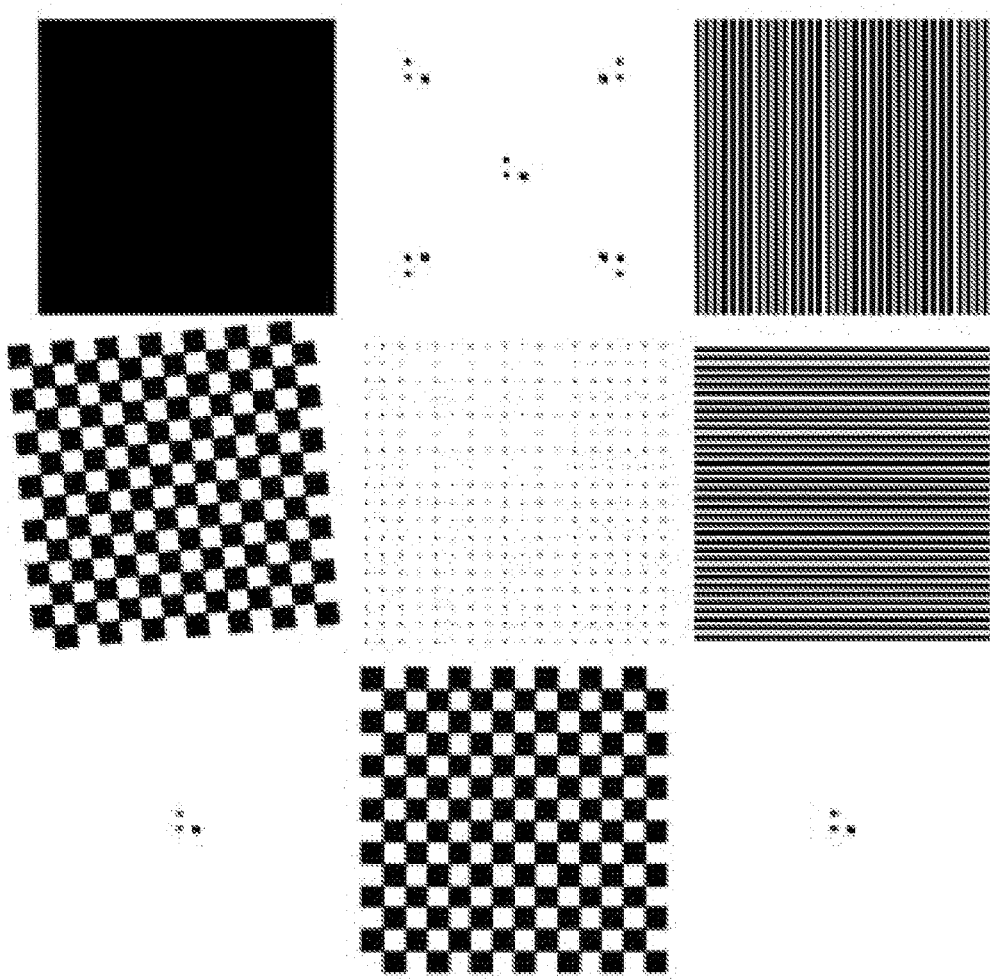
FIGS. 4(A)-4(B) depict non-limiting examples of pattern combinations for fluorescent layer 130 which can be utilized within a single calibration target 140.
Figure 4B:
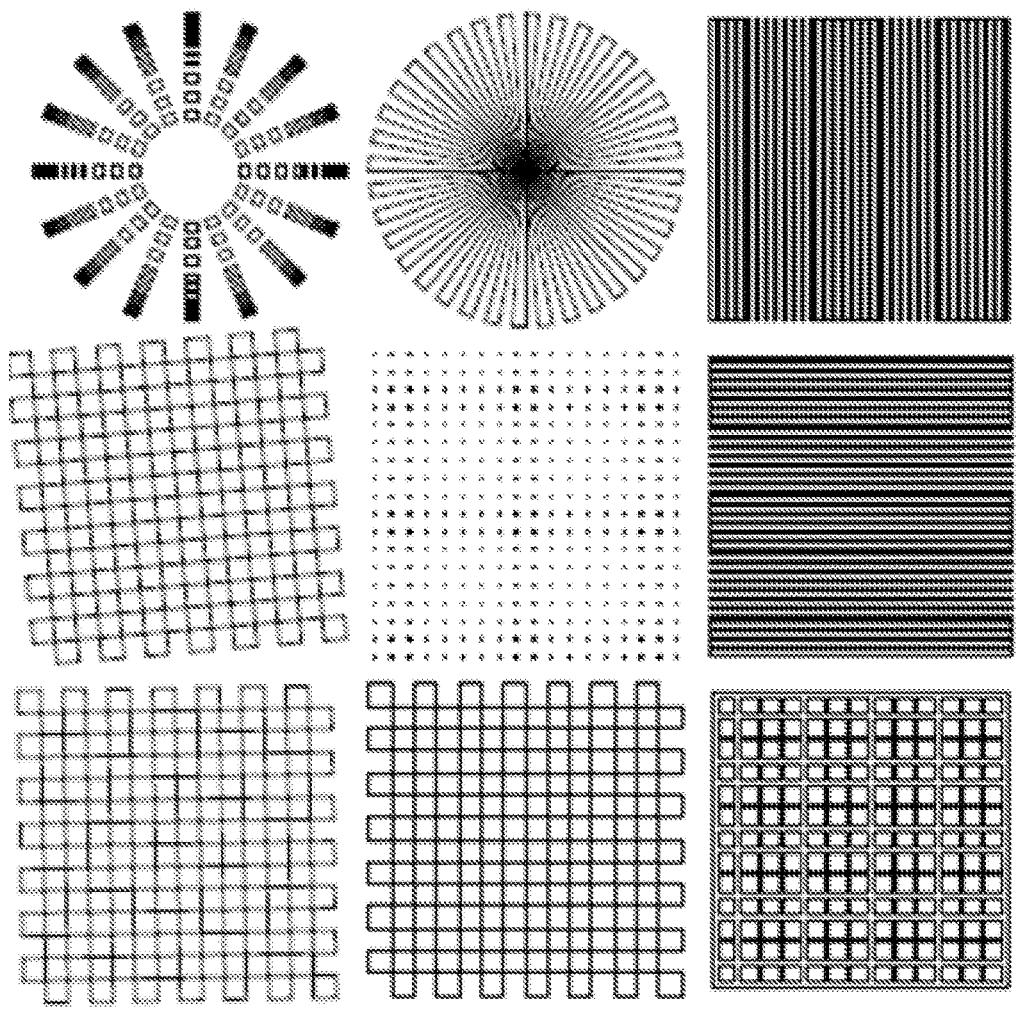

The pattern may be any appropriate pattern for facilitating calibration of the one or more fluorescent channels of the instrument and/or reflective channels of the instrument. Non-limiting examples of possible patterns are illustrated in FIGS. 3(A) through 3(L). Various embodiments may utilize a plurality of patterns within a single calibration target 140 with certain patterns repeated in different locations, repeated in different locations with alterations such as changes to size, shape, distribution and/or rotation, and/or in combination with other distinct patterns. Non-limiting examples of potential combinations of patterns are illustrated in FIGS. 4(A) and 4(B). Preferably, the patterns will be of a design with characteristics such as pattern variety, size, shape, and separation that aids in providing the relevant instrument with a calibration target 140 which has similar properties to the eventual fluorescently labeled material to be analyzed.

The formation of appropriate patterns allows calibration of the instrument in a manner that produces more accurate results of the material of interest. For example, if the expected fluorescent emissions to be captured by the instrument are 5 μm in diameter, a relevant embodiment of calibration target 140 would desirably possess at least some patterns within fluorescent layer 130 with structural features approximately 5 μm in diameter. Similarly, if the actual fluorescent labels are expected to be separated from each other by, for instance, 2 μm, the relevant embodiment of calibration target 140 would preferably have at least some structural features within fluorescent layer 130 which are separated by approximately 2 μm.

Many embodiments which utilize a reflective layer 120 will have the desired pattern(s) formed during step 240 in both the fluorescent layer 130 and the reflective layer 120. Formation of a calibration target 140 in this manner potentially assists in producing a dark (low signal) background if substrate 110 is also properly selected. With respect to the created pattern(s) within fluorescent layer 130, a dark background for corresponding fluorescent channels of the instrument will be provided if substrate 110 is selected from materials such that any fluorescent emissions at the relevant wavelengths are significantly lower than the fluorescent emissions from the fluorescent pattern within fluorescent layer 130. Furthermore, appropriate selection of materials for substrate 110 can also ensure that a low background signal is produced when reflective layer 120 is utilized with the one or more reflective channels of the instrument.

Creating the pattern in both the fluorescent layer 130 and reflective layer 120 may provide additional benefits in certain embodiments as well. For example, certain techniques utilized to create the patterns may not be completely precise with respect to the depth of the material removed from the layers deposited on substrate 110, such as fluorescent layer 130, reflective layer 120 and any spacing layers 150. Thus, if the entirety of fluorescent layer 130 and/or reflective layer 120 is not completely removed from desired areas of the pattern, any residue from each may contribute to undesirable background signal. Therefore, certain embodiments will employ the desired pattern creation technique to create the patterns at a depth that extends slightly beyond the expected combined thickness of reflective layer 120, fluorescent layer 130 and any spacing layers 150 which have been utilized. This will often result, depending on the technique, in a slight removal of material from substrate 110, but provides the benefit of facilitating a darker background for the resulting calibration through the complete elimination of reflective layer 120, fluorescent layer 130 and any spacing layers 150 within the desired areas of substrate 110. Accordingly, design of calibration targets 140 which are compatible with different fluorescent excitation/emission spectra, various instruments, and/or the inclusion of a reflective layer can greatly facilitate the complete calibration of all optical channels and related aspects of the relevant instrument with a limited number of types of calibration target 140, or more preferably with a single type of calibration target 140.

Figure 5A:
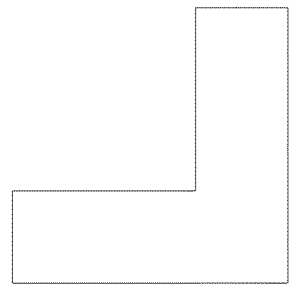
FIGS. 5(A)-5(B) depict non-limiting examples of patterns which can be created within reflective layer 120, and in some embodiments, fluorescent layer 130, in formatting fiducial markers on calibration target 140.
Figure 5B:
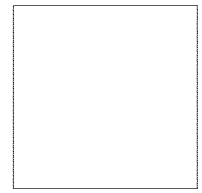
Figure 5C:
FIGS. 5(C)-5(D) depict examples of pattern combinations which can be utilized with a single calibration target 140.
Figure 5C:
Figure 5C:
Figure 5C:
Figure 5D:
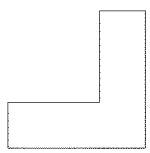
Figure 5D:
Figure 5D:
Figure 5D:
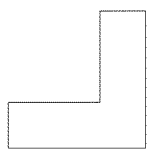
Figure 6A:
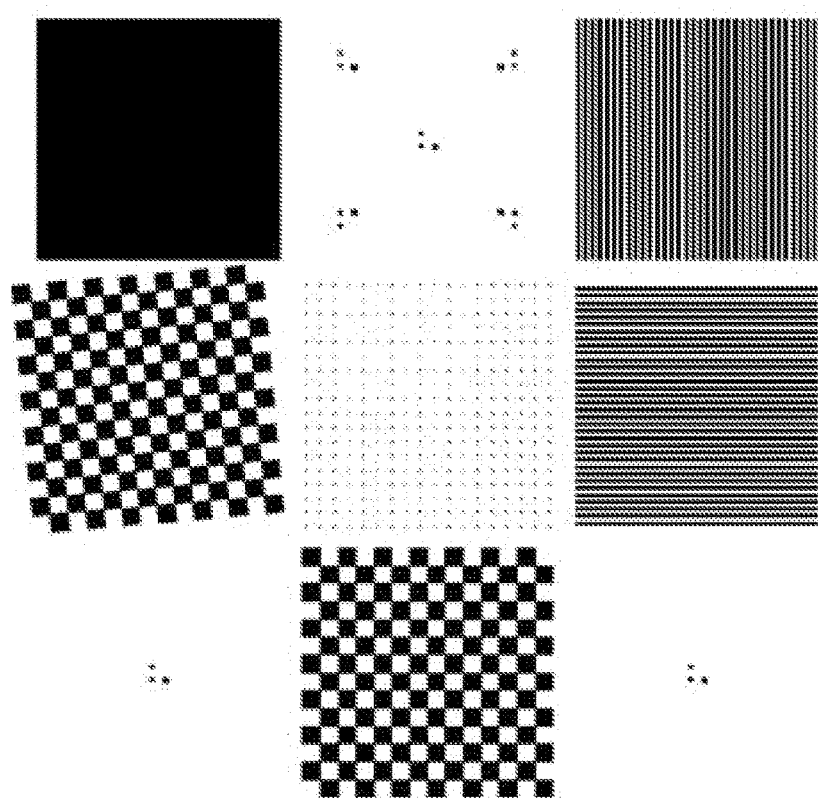
FIGS. 6(A)-6(B) depict non-limiting examples of pattern combinations which possess both patterns for fluorescent layer 130 and patterns for fiducial markers from reflective layer 120.
Figure 6B:
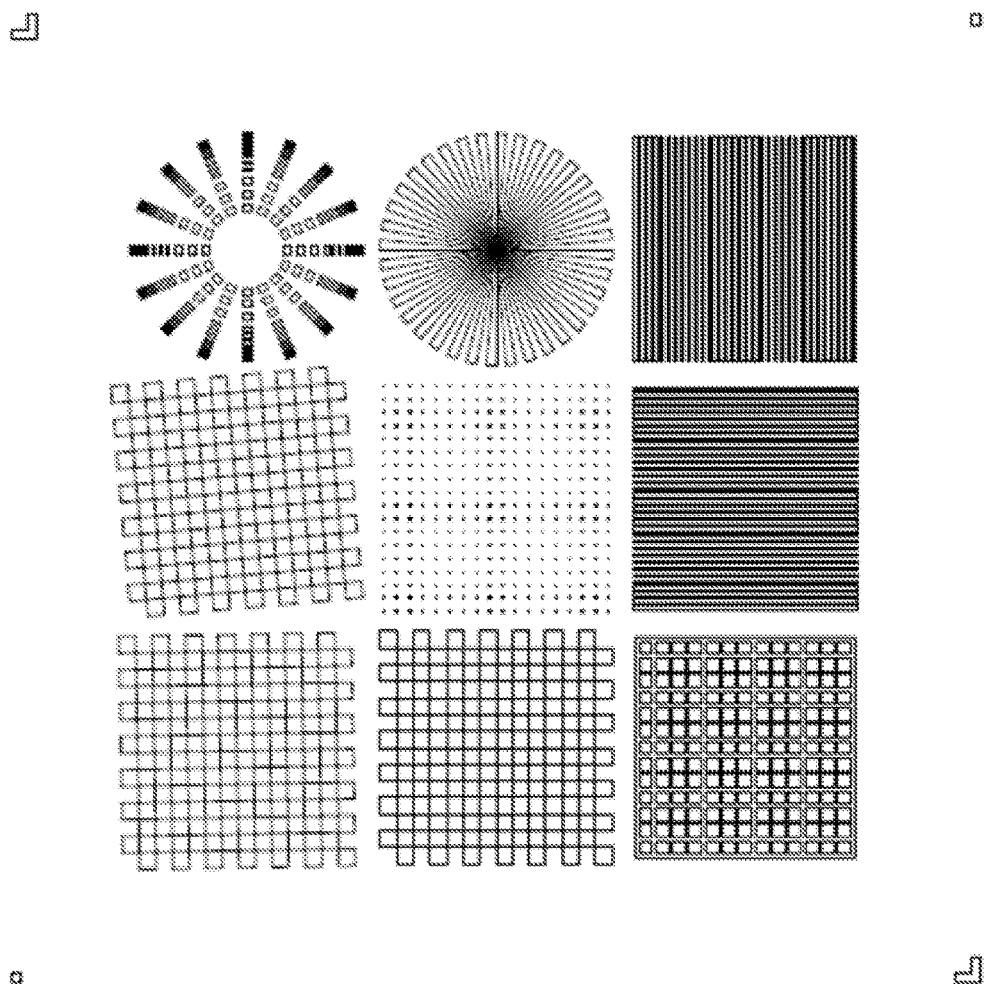

Embodiments which combine a reflective layer 120 with a fluorescent layer 130 may create additional patterns for calibration target 140 in addition to the patterns created for use with the fluorescent layer 130 and any relevant fluorescent channels of the instrument. For example, functions such as positional alignment and calibration of optical components, auto-focusing during illumination and/or imaging, and positional adjustments to the labeled material (or the substrate with which the labeled material is associated) often utilize one or more fiducial markers, such as borders or shapes placed in known locations (e.g., corners). Non-limiting examples include the illustrative shapes in FIGS. 5(A) and 5(B). Certain embodiments may use one type of fiducial, or combinations of types, as illustrated in FIGS. 5(C) and 5(D) respectively. Thus, the possible pattern combinations discussed above and illustrated in FIGS. 4(A) and 4(B) respectively can be combined with fiducial patterns to create a reflective layer 120 and a fluorescent layer 130 on substrate 110 as depicted in FIGS. 6(A) and 6(B).

In such combination embodiments, it is generally preferred to simplify the manufacturing process by forming the desired pattern for both the fluorescent calibration and the reflective calibration at the same time within step 240. Thus, the resulting structural features on substrate 110 would have both a reflective layer 120 with a fluorescent layer 130 positioned on top of reflective layer 120. While such a manufacturing process is more efficient, it is important to consider this structural relationship when designing such an embodiment, as fluorescent layer 130 (as well as a possible spacing layer 150) must not reduce the reflectance of reflective layer 120 to a degree where effective use of the fiducial markers is lost given the optical characteristics of the relevant instrument. Furthermore, the reflectance from reflective layer 120 must not significantly disrupt the detected fluorescence from fluorescent layer 130 at the relevant wavelengths during excitation of fluorescent layer 130 to a degree which interferes in accurate calibration of the one or more fluorescent channels of the instrument. Proper consideration of these factors, however, allows embodiments where all desired layers can be deposited upon substrate 110, followed by the formation of the desired patterns for reflective and fluorescent use in a single step.

Figure 7:
FIG. 7 depicts a non-limiting example of a pattern suitable to create a large quantity of calibration targets from a single substrate 110 with a reflective layer 120 and fluorescent layer 130, from which can be separated individual calibration targets 140 for subsequent use.

The above processes can be expanded, as illustrated in FIG. 7, to create a large quantity of calibration targets 140. Depending upon the desired number of calibration targets and the manufacturing process utilized, dozens, hundreds, or thousands of calibration targets can be created simultaneously. For example, FIG. 7 depicts 289 calibration targets. The quantity, of course, can be adapted to whichever format may be most convenient based upon factors such as the exact size and format of the calibration targets 140, the particular manufacturing techniques involved, etc. After manufacturing, these calibration targets 140 can then be separated from one another for use with various instruments.

After separation, some calibration targets 140 may be suitable for use directly with the relevant instrument. For example, if substrate 110 is a glass slide and the relevant instrument analyzes fluorescently labeled materials on glass slides, then corresponding embodiments of calibration target 140 may simply be used directly with the instrument. Other calibration targets 140, however, may need to be combined with other components before use with an instrument because of, for example, size and shape compatibility with the instrument or physical or chemical handling concerns. A non-limiting example of such a combination is use of calibration target 140 with a GeneChip® Array Cartridge (Affymetrix, Inc., Santa Clara, Calif.), non-limiting variations of which are described within U.S. Pat. Nos. 5,945,344; 6,140,044; 6,399,365; 6,551,817; and 6,733,977 to Besemer et al.

Figure 8A:
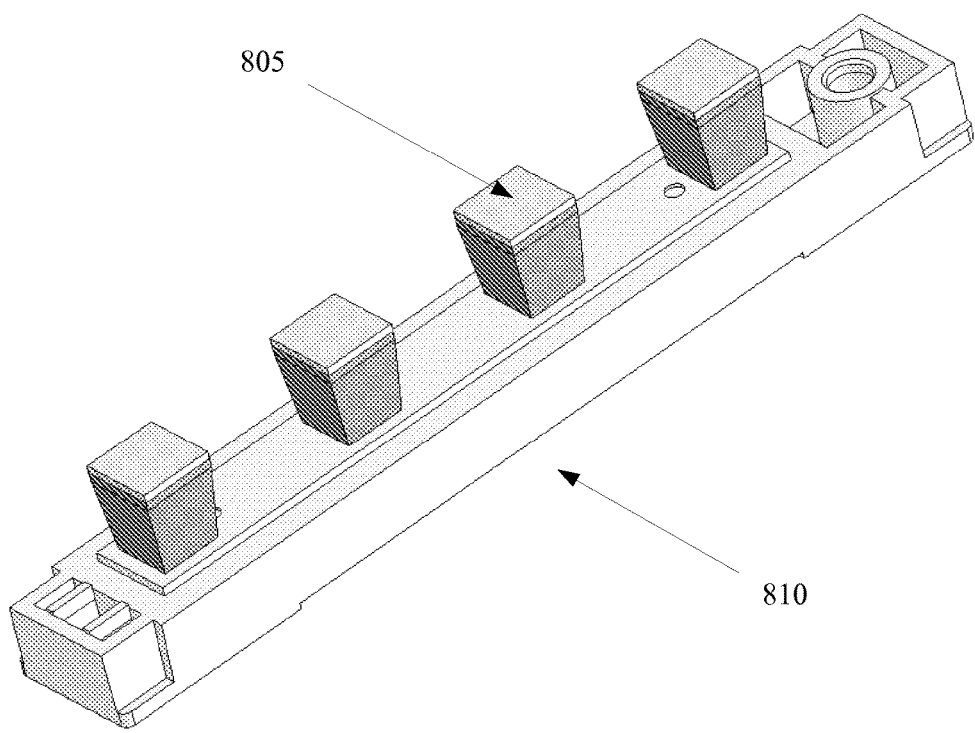
FIG. 8(A) depicts four pegs 805 mounted on a sensor strip 810, with the potential for all or some of the pegs 805 to possess a calibration target 140.
Figure 8B:
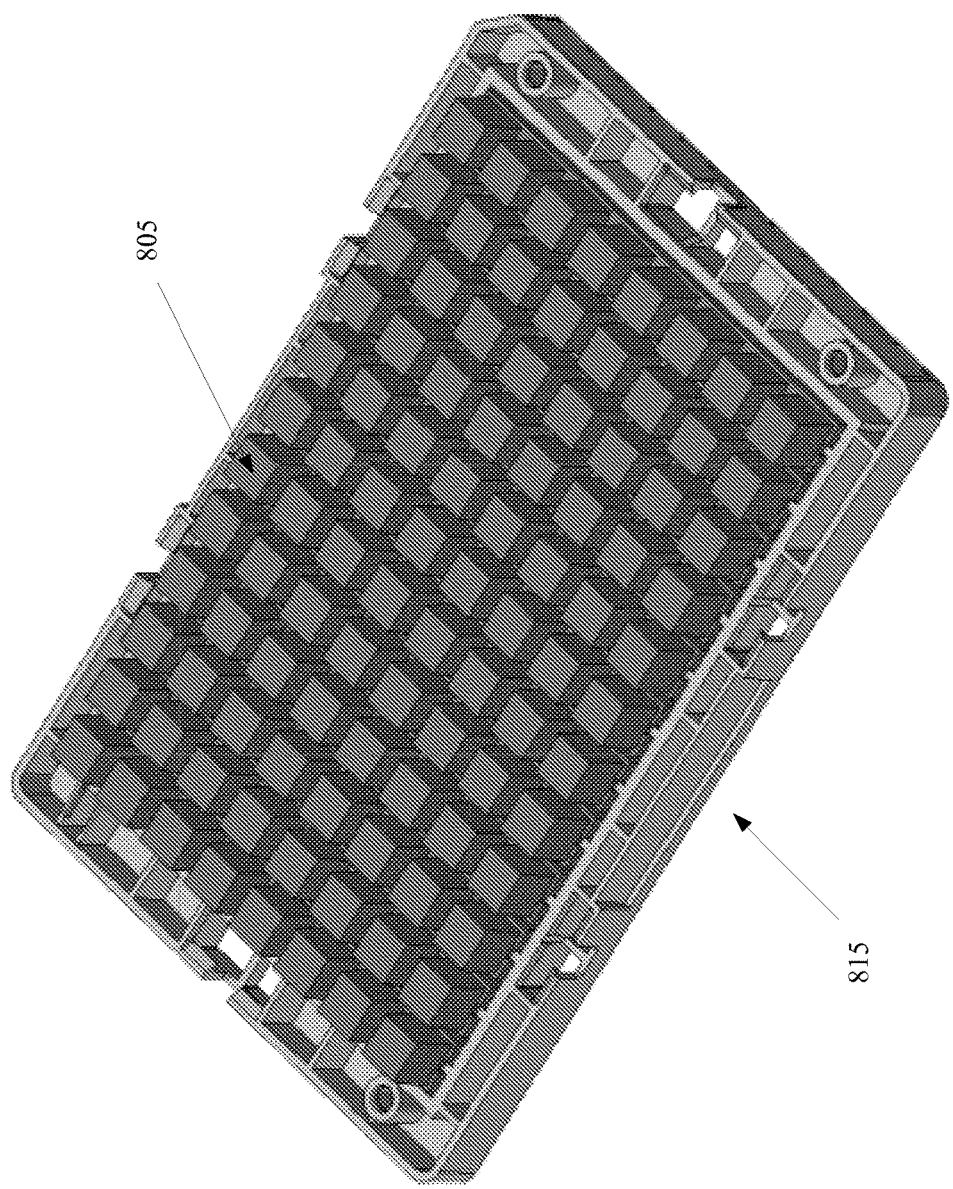
FIG. 8(B) depicts ninety-six pegs 805 mounted on a sensor plate 815, with the potential for all or some of the pegs 805 to possess a calibration target 140.

Calibration target 140 may also be mounted upon protrusions such as pegs for subsequent use with the instrument. U.S. Pat. No. 6,660,233 to Coassin et al. describe the detection of fluorescently labeled targets on pegs, and in some embodiments calibration target 140 is suitable for use in such systems. Use of multiple pegs within a single sensor plate or strip is described in U.S. patent application Ser. Nos. 11/243,621 and 11/347,654 to Yamamoto et al. Additional related applications include U.S. patent application Ser. Nos. 12/963,593 and 13/157,268 to Shirazi et al. Such plates and strips allow, for example, for more samples to be analyzed during a given time period. As illustrative non-limiting examples, FIG. 8(A) depicts an embodiment with a sensor strip 810 of four pegs 805 while FIG. 8(B) depicts an embodiment with a sensor plate 815 of ninety-six pegs 805. While a calibration target 140 may be placed on each and every peg within a particular plate or strip, such placement is not normally necessary for a precise and accurate calibration for many instruments. For example, certain embodiments of strips 810 may utilize one or two calibration targets 140 while certain embodiments of plates 815 may utilize, for instance, 1-10 calibration targets 140. Certain embodiments of plates 815 place calibration targets 140 at the borders of plate 815, such as at the four corner pegs of plate 815, with one or more calibration targets 140 placed more centrally within the assembly of pegs 805, or a combination of the two placements. The pegs of the strips 810 or plates 815 which do not possess calibration targets 140 may simply be left blank if calibration target 140 will only be used to calibrate the relevant instruments.

In other embodiments, strips 810 or plates 815 utilize calibration targets 140 in combination with the actual fluorescently labeled material of interest. For example, some embodiments utilize calibration targets 140 in combination with nucleic acid probe arrays designed to hybridize with a nucleic acid sample. Use of calibration targets 140 in this manner facilitates calibration of the relevant fluorescent channels of the instrument each time a particular fluorescently labeled material of interest is analyzed. While such continual calibration may not normally be required for many instruments, certain assays or experiments which require especially consistent and accurate results with respect to expected performance baselines can be improved by the use of one or more calibration targets 140 in combination with the fluorescently labeled materials of interest.

Figure 9:
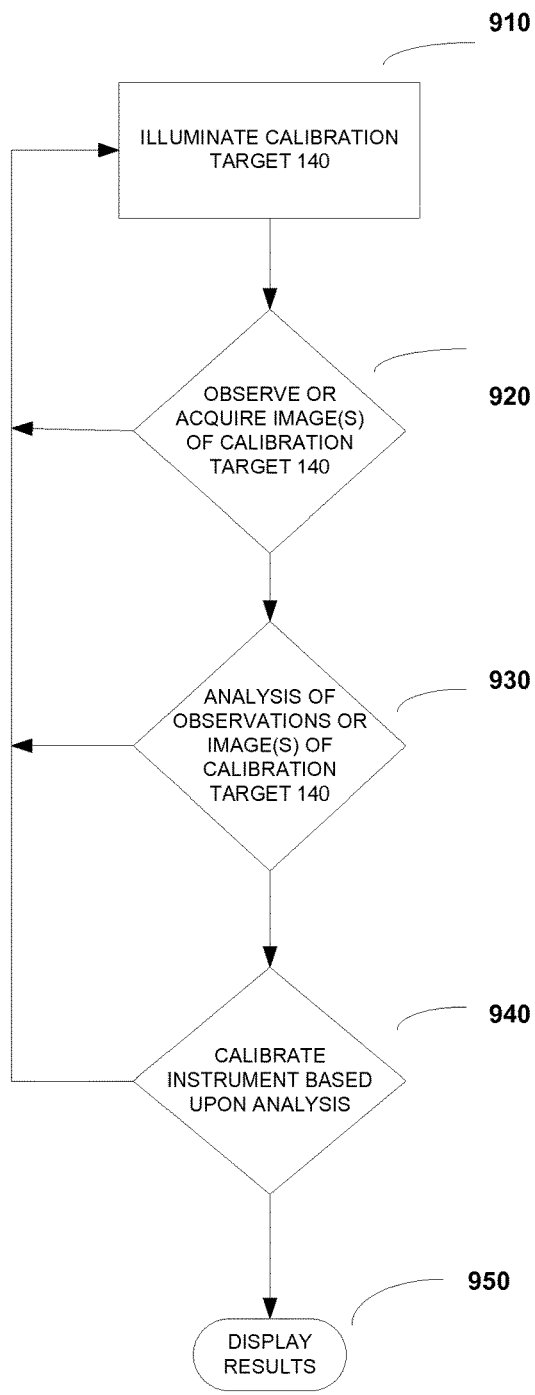
FIG. 9 depicts a flow chart illustrating the process with which certain embodiments of calibration target 140 will be utilized with instruments for calibration of one or more fluorescent channels, and optionally one or more reflective channels, through use of calibration target 140.

Subsequent use of calibration target 140 will vary depending on the embodiment and the relevant instrument, but certain embodiments may follow the flowchart depicted in FIG. 9. In step 910, calibration target 140 is illuminated by the relevant instrument to be calibrated. Thus, the type of illumination will depend on the characteristics of the instrument with respect to factors such as the source type (e.g., light emitting diodes, lasers, lamps), duration of illumination, the number of sources, the use of various optical components affecting the output illumination (e.g., filters, beam splitters) and other factors known in the art. For more effective calibration, the characteristics of illumination in step 910 will be tailored with respect to factors such as the properties of the particular type of calibration target 140, and desirably the fluorescently labeled material that will be subsequently analyzed by the instrument after calibration. In many embodiments, the illumination and overall instrument will be controlled, at least in part, by a computer, often following instructions stored within computer code and/or directed through input commands. In some applications, the illumination may be repeated one or more times, at the same or different wavelengths, depending upon the properties of the calibration target (e.g., whether the calibration target possesses a reflective layer 120 or fiducial markers, whether the calibration target is designed to simulate a plurality of different fluorophores) and the instrument (e.g., whether multiple different fluorescent channels are utilized).

Step 920 comprises the observation of calibration target 140 after illumination, and/or the acquisition of one or more images of at least a portion of calibration target 140, or in some embodiments the entirety of calibration target 140. Observation and acquisition of images can also be achieved by any suitable means known in the art (e.g., fluorescent microscopes including confocal, inverted, and total internal reflection fluorescence microscopes, a charge-coupled device (CCD) or variants such as electron-multiplying CCD or frame transfer CCD, or by a complementary metal-oxide-semiconductor (CMOS) approach such as an active pixel sensor), and will depend upon the embodiment and the particular instrument. If one or more images are acquired, many embodiments will store the images, for example on an associated computer on a computer-readable medium (e.g., hard drive, USB drive) or stored on an associated network server.

Depending upon the embodiment, steps 910 and 920 may be repeated one or more times. For example, the instrument may illuminate the reflective layer 120 as positioned within fiducials (e.g., the fiducials illustrated in FIGS. 5(A)-5(D)) for purposes such as auto-focusing and/or calibration of the one or more reflective channels of the instrument before subsequent illumination of one or more patterns within fluorescent layer 130 and calibration of the one or more fluorescent channels. In the non-limiting examples illustrated in FIGS. 6(A)-6(B), this may involve illumination and image acquisition of the four fiducial markers in the four corners of calibration target 140 before illumination and acquisition of the nine sets of patterns within the center of calibration target 140. Furthermore, many embodiments of calibration target 140 are optimally used with different illumination wavelengths or ranges of wavelengths with respect to the one or more reflective layers 120 and the one or more fluorescent layers 130. Thus, in addition to repeating step 910 for illumination of different portions of calibration target 140, other embodiments may repeat the illumination at different wavelengths while illuminating all or part of calibration target 140. Within the embodiments utilizing one or more fluorescent layers 130 for calibration of the instrument with respect to a plurality of fluorescent channels at one or more wavelengths or ranges of wavelengths (e.g., for calibration of an instrument that will be utilized with two or more types of fluorescent labels, with each type possessing a range of wavelengths for excitation and/or emission that are at least partially distinct from one another, or that are entirely non-overlapping inherently or after the use of appropriate filters), the fluorescent layers 130 may require multiple illuminations from one or more light sources at one or more wavelengths or ranges of wavelengths (e.g., use of different light emitting diodes at different wavelengths, use of different excitation filters with a lamp).

Step 930 comprises analysis of the observations or the acquired image(s) of calibration target 140. In many applications, a software program will analyze the observations and/or images for various aspects including, for example, uniformity, contrast, and emission signal strength, often by comparing these aspects quantitatively to pre-established criteria. The pre-established criteria can be stored on a computer for access by the program, and in certain applications is updated or is otherwise capable of editing by an automatic or manual process. The comparison can include, for example, whether a particular aspect of the acquired data is within a certain percentage range of the pre-established criteria. Certain applications also provide pass/fail calls based upon these aspects and criteria with respect to the general calibration analysis (e.g., instrument is in need of further calibration) or with respect to certain aspects (e.g., a lower than expected level of emissions is being detected for a particular illumination wavelength and a specific detection filter). The pass/fail call determinations may subsequently be stored in memory for subsequent use and/or presentation to a user. The application may be a component of the routine analysis platform for the instrument, or may be a supplemental application utilized, for example, during manufacturing quality control tests or during service maintenance and repair tests. As with steps 910 and 920, certain instruments and applications may repeat the analysis within step 930 one or more times after one or more subsequent repetitions of steps 910 and/or 920 (e.g., repeating the analysis for the patterns within fluorescent layer 130 after analysis of the fiducial markers of reflective layer 120).

Certain embodiments may additionally employ step 940, where the instrument is calibrated based upon the analysis of step 930. Depending upon the instrument and controlling software, certain applications may additionally utilize the analysis results to adjust the aspects of the process, such as positional adjustments (e.g., translating, rotating, tilting the instrument and/or calibration target 140 for more optimal performance), illumination adjustments (e.g., adjusting the focus, duration or wavelength of illumination), or adjustments to the observation of fluorescent emissions or the image acquisitions of the emissions (e.g., filter or focusing adjustments, adjustments to the relevant image capture device such as a CCD or CMOS device). Furthermore, certain applications will additionally analyze any fail calls resulting from step 930 to provide additional diagnostics and guidance as to required adjustments or component replacements based upon, for example, substantial discrepancies between the observations or acquired image(s) and the pre-established criteria. In an additional embodiment, these applications can also alert a user through, for example, a graphical user interface, e-mail, text message, or instant message, that one or more components require further testing, calibration, and/or replacement, as depicted in step 950.

III. Examples

Figure 10A:
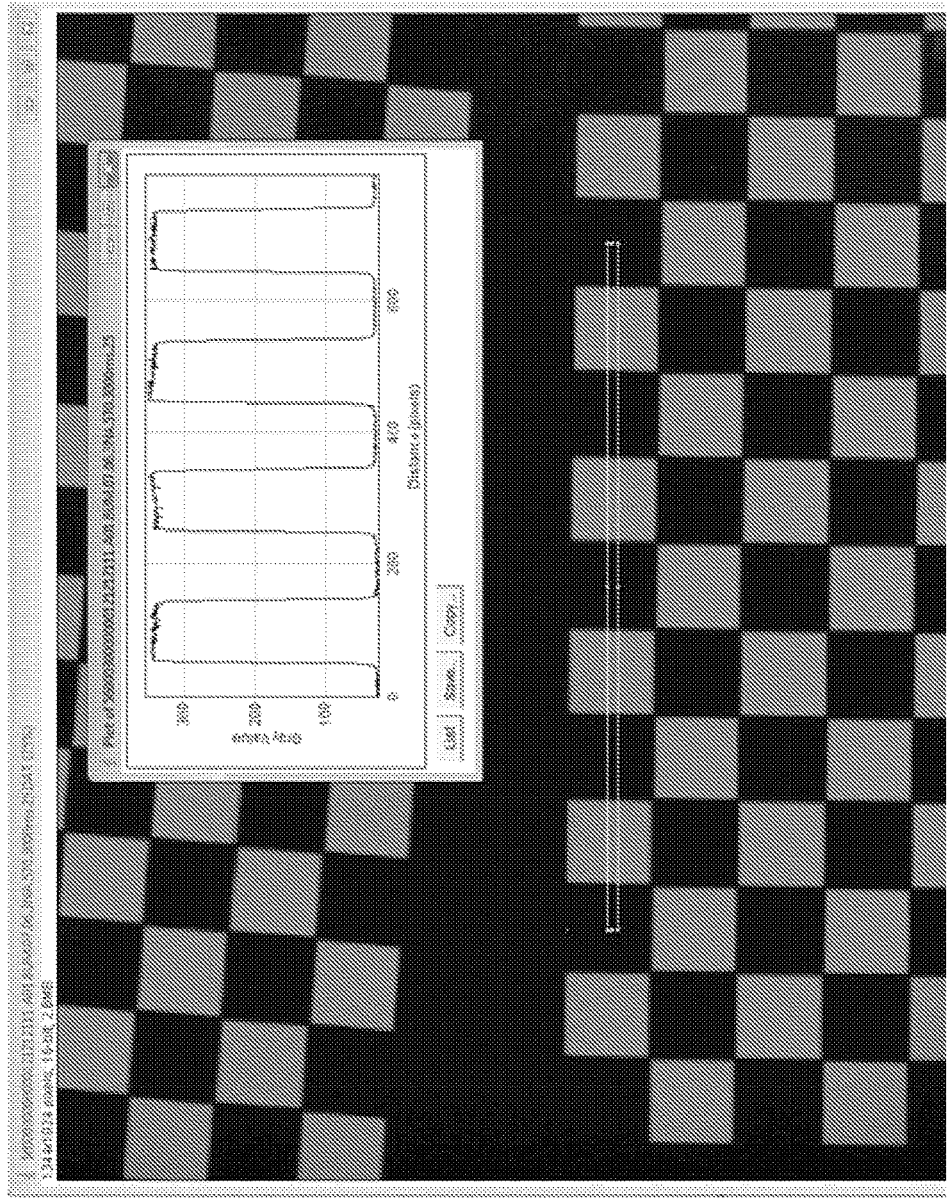
FIGS. 10(A) and 10(B) depict images obtained by scanning calibration targets 140 with a GeneAtlas® Scanner (Affymetrix, Inc., Santa Clara, Calif.).
Figure 10B:
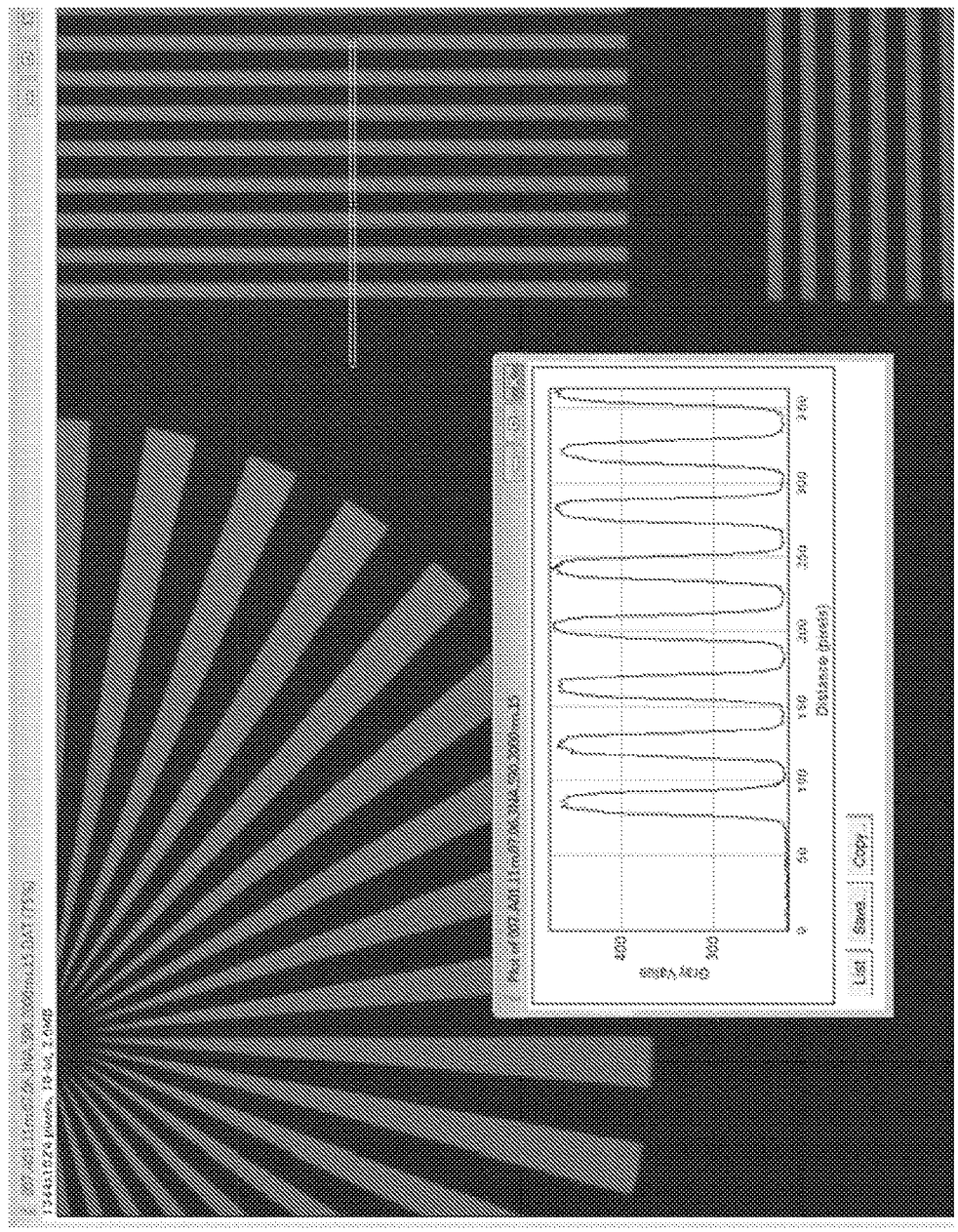

The images shown in FIGS. 10(A) and 10(B) were obtained from use of a calibration target 140 possessing a fluorescent layer 130 with patterns such as those illustrated within FIGS. 4(A) and 4(B). The calibration target 140 comprised a substrate 110 of fused silica, a reflective layer 120 of chromium with a thickness of 0.1 µm, and a fluorescent layer of AZ® photoresist (AZ Electronic Materials, Stockley Park, Middlesex, United Kingdom) with a thickness of 0.5 µm. The resulting calibration targets 140 were mounted on pegs, and scanned with a GeneAtlas® Scanner (Affymetrix, Inc., Santa Clara, Calif.) utilizing a 530 nm light emitting diode for illumination and a CCD camera for imaging, with a resolution of 1 µm and a digital resolution of 12 bits. The images were obtained after an exposure time of 3000 ms for the calibration target 140 in FIG. 10(A) and 2000 ms for the calibration target 140 in FIG. 10(B), while the fluorescence detection wavelength for both images was 590 nm±20 nm.

It is to be understood that the above description, including any examples provided herein, is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herein by reference in their entirety for all purposes.

What is claimed is:

1. A method of evaluating fluorescence detection performance by a fluorescent microscopy instrument comprising a fluorescent channel and a reflective channel, the method comprising:

illuminating a calibration target, wherein the calibration target comprises a substrate, a reflective layer, and a fluorescent layer, and wherein the fluorescent layer is illuminated with light configured to produce fluorescent emissions, and the reflective layer is illuminated with light configured to produce reflective illuminations;

detecting the fluorescent emissions with the fluorescent channel;

detecting the reflective illuminations with the reflective channel; and analyzing the fluorescent emissions and the reflective illuminations with a computer, wherein the computer comprises a computer software program, and wherein analyzing comprises comparing the fluorescent emissions and the reflective illuminations to one or more pre-established criteria.

2. The method of claim 1, wherein the fluorescent layer comprises one or more fluorescent materials formed into one or more patterns.

3. The method of claim 2, wherein the fluorescent layer comprises photoresist.

4. The method of claim 1, wherein the fluorescent microscopy comprises at least two fluorescent channels.

5. The method of claim 4, wherein illuminating the calibration target comprises a first illumination with light comprising a first set of one or more excitation wavelengths and a second illumination with light comprising a second set of one or more excitation wavelengths, and wherein the first set of one or more excitation wavelengths and the second set of one or more excitation wavelengths are at least partially non-overlapping.

6. The method of claim 5, wherein the first illumination produces a first set of emissions from the fluorescent layer and the second illumination produces a second set of emissions from the fluorescent layer, and wherein the computer analyzes the first set of emissions to evaluate a first fluorescent channel and the second set of emissions to evaluate a second fluorescent channel.

7. The method of claim 6, wherein the first set of emissions and the second set of emissions comprise different emission spectra.

8. The method of claim 6, wherein the fluorescent layer comprises one or more fluorescent materials such that the first set of emissions possess emission properties similar to a first type of fluorophore and the second set of emission possess emission properties similar to a second type of fluorophore.

9. The method of claim 2, wherein the fluorescent layer comprises a first fluorescent material and a second fluorescent material, and wherein the first fluorescent material and second fluorescent material possess different excitation and emission properties.

10. The method of claim 1, wherein the method additionally comprises:
adjusting the positional alignment of the calibration target with respect to the fluorescent microscopy instrument based upon detected reflection from the reflective layer.

11. The method of claim 10, wherein the reflective layer comprises one or more reflective materials formed into one or more patterns, and wherein the fluorescent layer comprises one or more fluorescent materials formed into one or more patterns identical to the one or more patterns of the reflective materials.

12. The method of claim 10, wherein one or more patterns of the one or more reflective materials are used by the fluorescent microscopy instrument as fiducial markers for adjusting the positional alignment.

13. An apparatus for calibration of a fluorescent microscopy instrument, the apparatus comprising:
a substrate;
a reflective layer deposited on the substrate, wherein the reflective layer comprises one or more reflective materials formed into one or more patterns;
a fluorescent layer deposited on the reflective layer, wherein the fluorescent layer comprises one or more fluorescent materials formed into one or more patterns;
a fluorescent channel which is configured to detect fluorescent emissions generated from the fluorescent layer; and
a reflective channel which is configured to detect reflective illuminations generated from the reflective layer.

14. The apparatus of claim 13, wherein the fluorescent layer comprises photoresist.

15. The apparatus of claim 13, wherein the one or more fluorescent materials are selected such that different emission spectra are produced upon illumination with different excitation spectra.

16. A method of manufacturing an apparatus for calibration of a fluorescent microscopy instrument, the method comprising:
providing a substrate;
depositing a reflective layer on the substrate;
depositing an optically transparent spacing layer on the reflective layer;
depositing a fluorescent layer on the substrate, wherein the fluorescent layer comprises one or more fluorescent materials; and
creating one or more patterns in the reflective layer and the fluorescent layer.

17. The method of claim 16, wherein the one or more patterns in the reflective layer and the fluorescent layer are identical, and wherein the one or more patterns are created simultaneously.

18. The method of claim 16, wherein the fluorescent layer comprises photoresist.

19. The method of claim 16, wherein the one or more fluorescent materials are selected such that different emission spectra are produced upon illumination with different excitation spectra.

* * * * *